(12) United States Patent
Agrawal

(10) Patent No.: US 9,532,907 B1
(45) Date of Patent: Jan. 3, 2017

(54) REUSABLE TAMPON APPLICATORS, METHODS OF MANUFACTURE, AND METHODS OF USE

(71) Applicant: THINX INC., New York, NY (US)

(72) Inventor: Miki Agrawal, Brooklyn, NY (US)

(73) Assignee: THINX Inc., New York, NY (US)

( * ) Notice: Subject to any disclaimer, the term of this patent is extended or adjusted under 35 U.S.C. 154(b) by 0 days.

(21) Appl. No.: 15/184,512

(22) Filed: Jun. 16, 2016

Related U.S. Application Data

(60) Provisional application No. 62/195,295, filed on Jul. 22, 2015.

(51) Int. Cl.
  *A61F 13/26* (2006.01)
  *A61F 13/20* (2006.01)

(52) U.S. Cl.
  CPC ......... *A61F 13/266* (2013.01); *A61F 13/2097* (2013.01)

(58) Field of Classification Search
  CPC .... A61F 13/20; A61F 13/202; A61F 13/2097; A61F 13/26; A61F 13/266; A61F 13/34
  See application file for complete search history.

(56) References Cited

U.S. PATENT DOCUMENTS

| | | | |
|---|---|---|---|
| 940,519 A * | 11/1909 | Eastman | A61K 9/0036 604/15 |
| 2,351,836 A * | 6/1944 | Popper | A61F 13/26 56/208 |
| D156,948 S | 1/1950 | Fisher | |
| 2,733,714 A * | 2/1956 | Haas | A61F 13/2051 604/14 |
| 3,204,635 A * | 9/1965 | Voss | A61F 13/26 604/14 |
| 3,895,634 A | 7/1975 | Berger et al. | |
| D250,049 S | 10/1978 | Hite | |
| D250,663 S | 12/1978 | Koch et al. | |
| 4,148,317 A | 4/1979 | Loyer | |

(Continued)

OTHER PUBLICATIONS

Playtex, "Tampon products," website available at: http://www.playtexplayon.com/products/gentle-glide Accessed on Jul. 27, 2014.

(Continued)

*Primary Examiner* — Kathryn E Ditmer
(74) *Attorney, Agent, or Firm* — American Patent Agency PC; Daniar Hussain; Xiaomeng Shi

(57) ABSTRACT

Disclosed are reusable tampon applicators, methods of use, and methods of manufacture thereof. A reusable tampon applicator comprises a cylindrical body, and a pusher for pushing a tampon through the cylindrical body during tampon insertion. The cylindrical body comprises a base opening at a distal end for inserting the tampon into a straight barrel connected to a convex apex at a proximal end. The convex apex comprises a slit opening for the tampon to pass through during tampon insertion. The slit opening extends from the proximal end to the distal end to form a full slit on a first lateral side of the cylindrical body; it further extends from the proximal end towards the distal end to form a partial slit on a second lateral side. Such reusable tampon applicators provide a hygienic and eco-friendly alternative to disposable tampon applicators.

19 Claims, 16 Drawing Sheets

(56) References Cited

U.S. PATENT DOCUMENTS

| | | | |
|---|---|---|---|
| 4,159,719 A * | 7/1979 | Haerr | A61M 31/00 |
| | | | 128/865 |
| 4,650,459 A | 3/1987 | Sheldon | |
| 4,699,610 A | 10/1987 | Hanano et al. | |
| 4,895,559 A * | 1/1990 | Shippert | A61B 17/12022 |
| | | | 604/15 |
| D415,565 S | 10/1999 | Hayes et al. | |
| 5,988,386 A | 11/1999 | Morrow | |
| D427,424 S | 7/2000 | Conway | |
| D432,784 S | 10/2000 | Conway | |
| 6,508,780 B1 * | 1/2003 | Edgett | A61F 13/26 |
| | | | 604/15 |
| D477,075 S | 7/2003 | Schoelling | |
| D484,681 S | 1/2004 | Eldon et al. | |
| 6,786,883 B2 * | 9/2004 | Shippert | A61F 13/26 |
| | | | 604/15 |
| D515,212 S | 2/2006 | Edgett et al. | |
| D516,716 S | 3/2006 | Weber et al. | |
| D517,210 S | 3/2006 | Weber et al. | |
| 7,137,995 B2 * | 11/2006 | Studin | A61F 2/12 |
| | | | 604/181 |
| D585,548 S | 1/2009 | Sargent et al. | |
| D612,940 S | 3/2010 | Edgett et al. | |
| D619,478 S | 7/2010 | Drewnowski et al. | |
| D626,650 S | 11/2010 | Edgett et al. | |
| 8,029,485 B2 | 10/2011 | Jensen | |
| D716,020 S | 10/2014 | Dunbar et al. | |
| D717,950 S | 11/2014 | Agrawal | |
| D719,653 S | 12/2014 | Agrawal | |
| D741,479 S | 10/2015 | Agrawal | |
| 2011/0275977 A1 * | 11/2011 | Watanabe | A61F 13/26 |
| | | | 604/15 |
| 2014/0155810 A1 * | 6/2014 | Buell | A61F 13/34 |
| | | | 604/16 |

OTHER PUBLICATIONS

Beautydeals, "Sprayco Microban Tampon Case," website available at: https://www.beautydeals.net/shop/details.html?id=13573 Accessed on Jul. 27, 2014.

The Find, "Tampon holder case," website available at: http://www.thefind.com/family/info-tampon-holder-case Accessed on Jul. 27, 2014.

TBOX, "Tampon Holder," website available at: http://tboxgirl.com/ Accessed on Jul. 27, 2014.

Kosmetik, "Lipstick holder tampon case," website available at: http://mocoloco.com/art/archives/005969.php Accessed on Jul. 27, 2014.

Tampax, "Tampax Tampons," website available at: http://www.tampax.com/en-us/products/pearl/tampax-pearl-active-regular-tampons.aspx Accessed on Jul. 27, 2014.

Playtex, "Tampon guide," website available at: http://www.playtexplayon.com/first-time-users/how-to-use Accessed on Jul. 27, 2014.

\* cited by examiner

BACK

SIDE

BOTTOM

FRONT

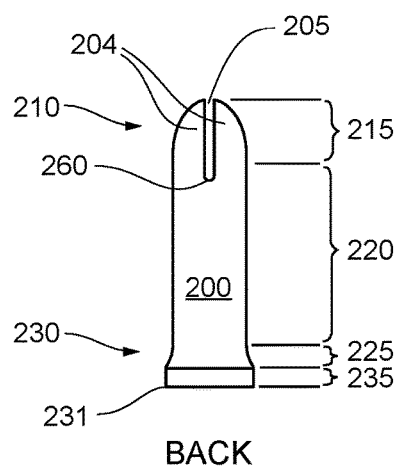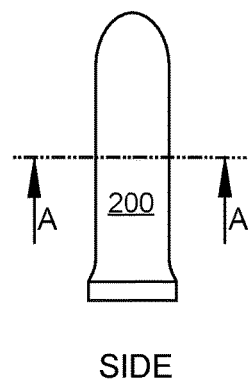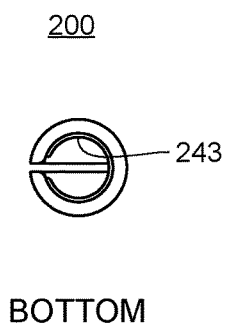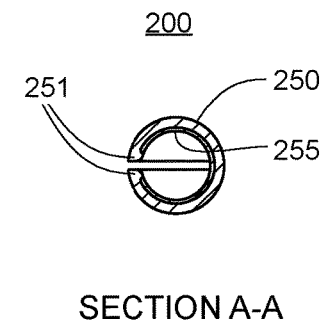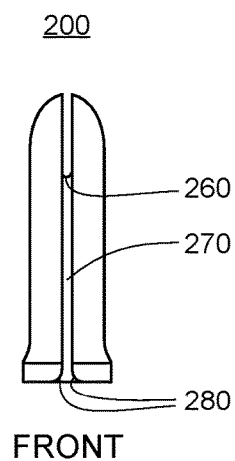

BACK

SIDE

BOTTOM

FRONT

BACK    FRONT

580

FRONT
ASSEMBLED

590

FRONT
ASSEMBLED

ASSEMBLED

ASSEMBLED

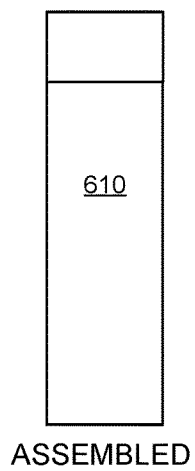
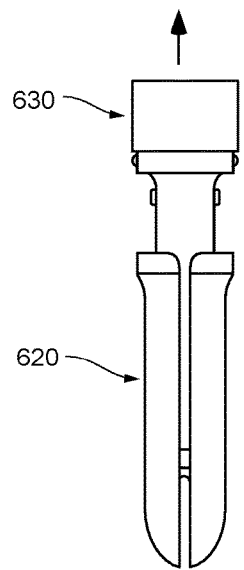
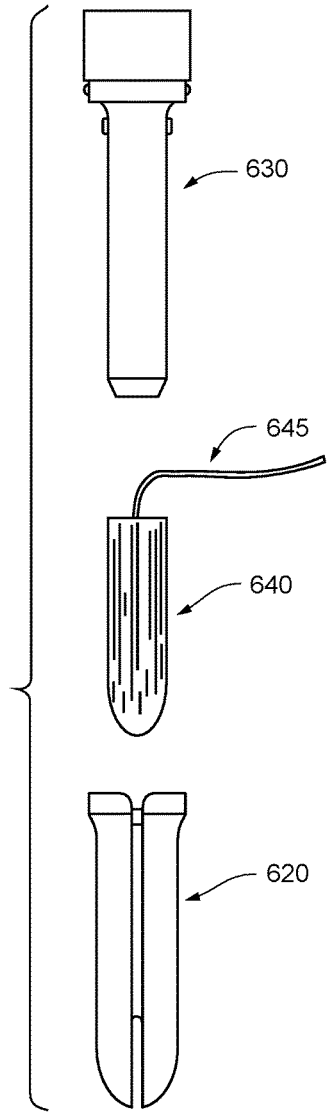
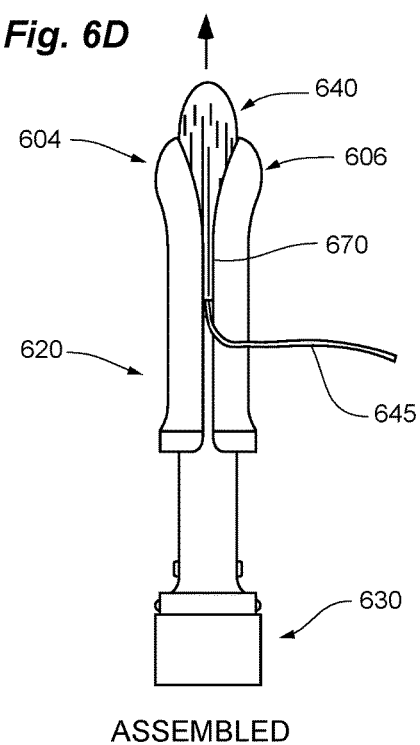
Fig. 6A  ASSEMBLED
Fig. 6B
Fig. 6C
Fig. 6D  ASSEMBLED

ASSEMBLED

BACK

*Fig. 8A*
*Fig. 8B*
*Fig. 8C*
*Fig. 8D*
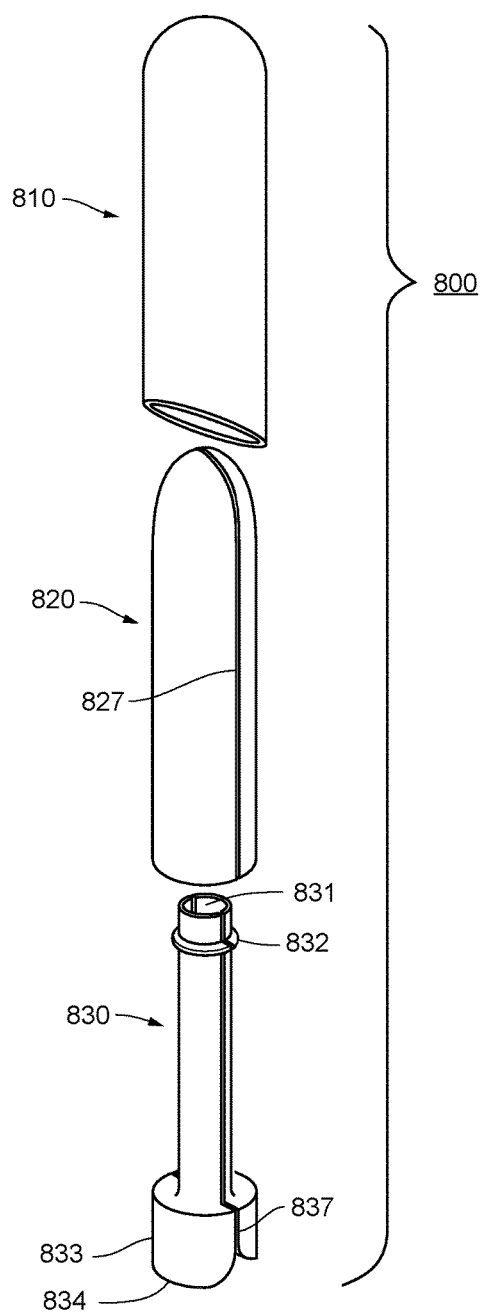
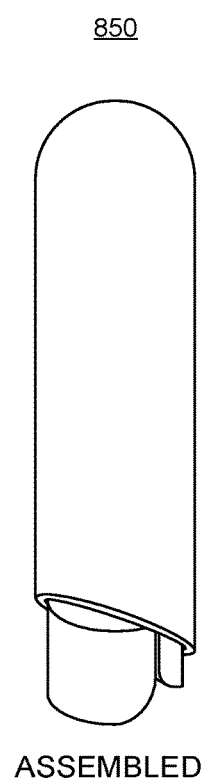
ASSEMBLED
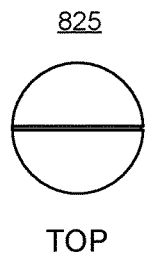
TOP
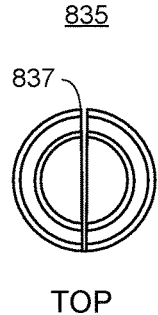
TOP

Fig. 9A
910
922
920
930
900
Fig. 9B
950
ASSEMBLED
Fig. 9C
925
928
TOP
Fig. 9D
935
TOP
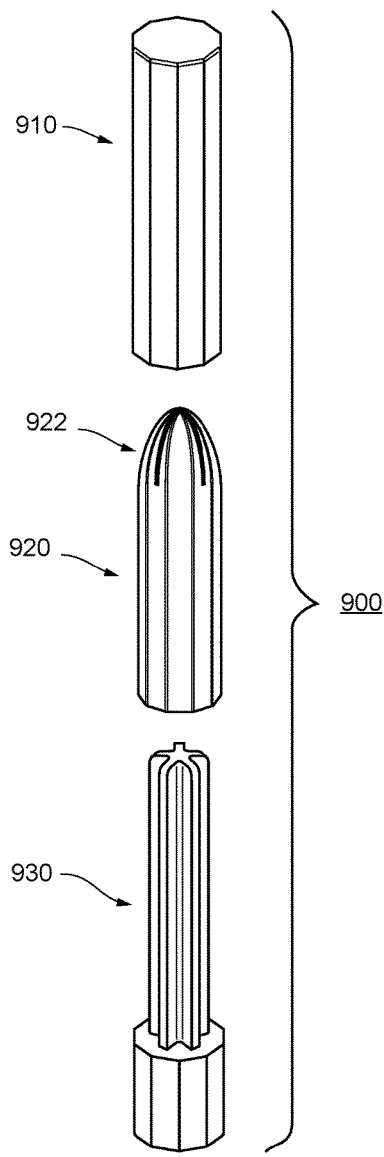
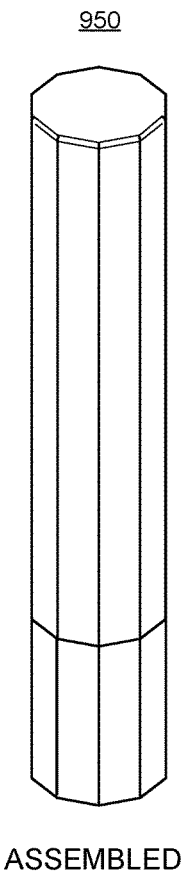
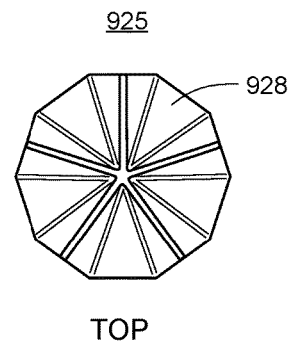
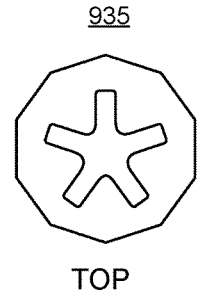

1140 RIGHT SIDE

1150 FRONT

1152 TOP

1154 BOTTOM

1160  LEFT SIDE

1162  SECTION A-A

1170  BACK

1172  SECTION B-B

RIGHT SIDE

SECTION A-A

FRONT

TOP

BOTTOM

FRONT

SECTION A-A

TOP

BOTTOM

REUSABLE TAMPON APPLICATORS, METHODS OF MANUFACTURE, AND METHODS OF USE

REFERENCE TO RELATED APPLICATIONS

This application is a non-provisional of and claims the benefit of provisional application having U.S. Ser. No. 62/195,295, filed on Jul. 22, 2015, and entitled "REUSABLE TAMPON APPLICATORS, METHODS OF MANUFACTURE, AND METHODS OF USE," the entire disclosure of which is hereby incorporated in its entirety herein.

NOTICE OF COPYRIGHTS AND TRADEDRESS

A portion of the disclosure of this patent document contains material which is subject to copyright protection. This patent document may show and/or describe matter which is or may become tradedress of the owner. The copyright and tradedress owner has no objection to the facsimile reproduction by anyone of the patent disclosure as it appears in the U.S. Patent and Trademark Office files or records, but otherwise reserves all copyright and tradedress rights whatsoever.

FIELD OF THE INVENTION

Embodiments of the present invention broadly relate to tampon applicators, and methods for manufacture and use of tampon applicators.

BACKGROUND OF THE INVENTION

The statements in this section may serve as a background to help understand the invention and its application and uses, but may not constitute prior art.

From soda bottles to shopping bags, blister packs to six pack rings, plastics are ubiquitous in our current disposable age. Accompanying the convenience of plastic use is the challenges of plastic waste management due to plastics' non-degradable nature. Every year, thousands of tons of plastic waste are washed ashore. Among those are hundreds of thousands of disposable tampon applicators, so common that they are even given the nickname "beach whistle." On average, twenty billion pads, tampons, and applicators enter the landfill annually. While pads and tampons may be made biodegradable, disposable plastic tampon applicators do not disintegrate easily.

Furthermore, disposable tampon applicators currently available on the market are mostly made of thin, cheap plastics that have undergone minimal molding and trimming to minimize production cost and reduce manufacturing complexity. Safety and hygiene issues can arise during tampon application as such low-quality disposable tampon applicators may pinch or even slice a user's internal tissues. In addition, no reusable tampon applicators are available today, thus users often resort to modifying single-use disposable applicators to fit washable tampons knitted or crocheted from cotton or other suitable materials, yet protrusions and/or depressions hidden within a disposable applicator often makes it difficult to wash with water or to clean with hygiene wipes after each use.

Therefore, in view of the aforementioned difficulties, there is an unsolved need for reusable tampon applicators, especially those that are safe to use, easy to clean and sustainable, thus helping protect the environment in a socially responsible way.

It is against this background that various embodiments of the present invention were developed.

BRIEF SUMMARY OF THE INVENTION

Embodiments of the present invention provide a sustainable, eco-conscious, economic, yet also convenient, comfortable, and hygienic alternative to disposable tampon applicators. Embodiments of the present invention include reusable tampon applicators, methods of manufacture of reusable tampon applicators, and methods of use thereof. Such reusable tampon applicators as described herein are manufactured of medical grade or food grade silicone, and made compact enough to fit into a woman's purse. In various embodiments, the silicone applicator body is soft at the tip but rigid in the tube area, utilizing a co-molding manufacturing process.

More specifically, one embodiment of the present invention is a reusable tampon applicator, comprising a hollow cylindrical body for holding a tampon for tampon application, and a pusher for telescopic insertion into the cylindrical body, and for pushing the tampon through the cylindrical body and a slit opening during tampon insertion. The cylindrical body comprises a distal end and a proximal end, and a base opening at the distal end for inserting the tampon into a straight barrel connected to a convex apex at the proximal end. The convex apex comprises a slit opening for the tampon to pass through during tampon insertion. The slit opening extends longitudinally from the proximal end to the distal end, through the straight barrel, to form a full slit on a first lateral side of the cylindrical body; the slit opening further extends longitudinally from the proximal end towards the distal end, through the straight barrel, to form a partial slit on a second lateral side of the cylindrical body, opposite to the first lateral side of the straight barrel. The partial slit is shorter in length along the cylindrical body than the full slit. The pusher comprises a distal end and a proximal end as well.

In some embodiments of the present invention, the reusable tampon applicator further comprises a case for telescopically enclosing the cylindrical body and the pusher.

In some embodiments of the present invention, the partial slit on the second lateral side of the cylindrical body extends into the straight barrel for a length between 2 mm and 5 mm. In some embodiments, the ratio of lengths between the partial slit and the full slit is between 1:10 and 2:7, between 2:7 and 1:3, or between 1:3 and 1:2.

In some embodiments, the cylindrical body comprises an outer medical grade or food grade silicone layer and an inner plastic support layer, wherein the outer layer extends fully over an exterior surface of the cylindrical body. In some embodiments, the inner layer extends partially over an interior lateral surface of the cylindrical body, wherein the inner layer is enclosed fully by the outer later. In some embodiments, the plastic support is made of a plastic material, wherein the plastic material is selected from the group consisting of ABS and Nylon. In some embodiments, the cylindrical body further comprises a transition portion and a base grip portion at the distal end, wherein an external diameter of the base grip portion is larger than an external diameter of the straight barrel. In some embodiments, the distal end of the cylindrical body comprises a flat base surface, for standing the cylindrical body on a flat surface.

In yet some embodiments, the pusher comprises at least one notch on an external lateral surface for securing the cylindrical body and the pusher while not in use. In some embodiments, the distal end of the pusher comprises a flat base surface, for standing the pusher on a flat surface. In some embodiments, the pusher comprises a main cylindrical portion, and a base grip portion at a distal end of the pusher, wherein an external diameter of the main cylindrical portion is smaller than an internal diameter of the base opening of the cylindrical body, and wherein an external diameter of the base grip portion is larger than an internal diameter of the base opening of the cylindrical body.

In another aspect, the present invention is a method for making a reusable tampon applicator, comprising the steps of bounding an inner plastic support layer and an outer medical grade or food grade silicone layer of a hollow cylindrical body, and forming a cylindrical pusher, for telescopic insertion into the cylindrical body, and for pushing a tampon through a slit opening during tampon application. The cylindrical body and the pusher of the reusable tampon applicator are embodied as described above.

Yet other aspects of the present invention include methods and processes comprising the steps described herein, and also include the processes and modes of operation of the systems, devices, and articles described herein. Other aspects and embodiments of the present invention will become apparent from the detailed description of the invention when read in conjunction with the attached drawings.

BRIEF DESCRIPTION OF THE DRAWINGS

Embodiments of the present invention described herein are exemplary, and not restrictive. Embodiments will now be described, by way of examples, with reference to the accompanying drawings. For purposes of clarity, not every component is labeled in every drawing. The drawings are not necessarily drawn to scale, with emphasis instead being placed on illustrating various aspects of the devices described herein.

FIGS. 2A, 2B, 2C, 2D, and 2E show back, side, bottom, sectional and front sides of a body for the reusable tampon applicator respectively, according to one embodiment of the present invention.

FIGS. 6A, 6B, 6C, and 6D illustrate a use of a reusable tampon applicator for disposing a tampon into the tampon applicator, and inserting the tampon into a user's body, respectively, according to one embodiment of the present invention.

FIGS. 8A and 8B show exploded and assembled views of a reusable tampon applicator respectively, according to a third embodiment of the present invention.

FIGS. 8C and 8D show respective top views of the exemplary reusable tampon applicator body and pusher in FIG. 8A.

FIGS. 9A and 9B show exploded and assembled views of a reusable tampon applicator respectively, according to a fourth embodiment of the present invention.

FIGS. 9C and 9D show respective top views of the exemplary reusable tampon applicator body and pusher in FIG. 9A.

DETAILED DESCRIPTION OF THE INVENTION

Figure 1A:
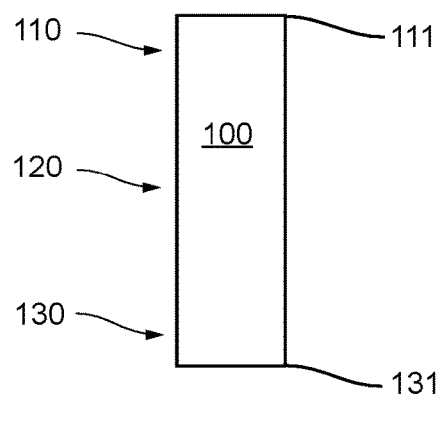
FIGS. 1A, 1B, 1C, and 1D show back, side, bottom, and front sides of a cover case for a reusable tampon applicator respectively, according to one embodiment of the present invention.
Figure 1B:
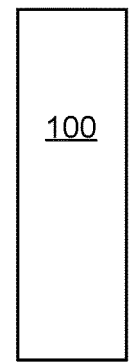

In the following description, for purposes of explanation, numerous specific details are set forth in order to provide a thorough understanding of the invention. It will be apparent, however, to one skilled in the art that the invention can be practiced without these specific details. In other instances, structures, devices, processes, and methods are shown using schematics, use cases, and/or diagrams in order to avoid obscuring the invention. Although the following description contains many specifics for the purposes of illustration, anyone skilled in the art will appreciate that many variations and/or alterations to suggested details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon, the invention.

Broadly, embodiments of the present invention relate to reusable tampon applicators, and methods and systems for manufacture, and methods of use of said tampon applicator devices. Such reusable tampon applicators are designed and developed to supplement, substitute, or replace disposable plastic or paper tampon applicators currently available today, providing a more eco-conscious, safe, and clean alternative to disposable plastic applicators.

More particularly, various embodiments of the present invention comprise one or more of a pusher or plunger, an applicator body, and an enclosing cover case, where the constituting components may be assembled telescopically and securely when not in use. While the pusher and the enclosing case may be formed in any suitable shape, the applicator body is cylindrical, and resembles a bullet or a lipstick tube in appearance, with a tube-shaped barrel extending from a distal end to a proximal end that curves into a convex apex. During tampon application, a single disposable or reusable tampon is placed inside the barrel from a base opening on the distal end of the cylindrical body, and pushed through the cylindrical body by the pusher or plunger, out from one or more intersecting slit openings on the apex located at the top of the cylindrical body. Once cleaned and tightly assembled, the reusable tampon applicator may be visually indistinguishable from a lipstick, thus allowing a user to handle and carry it with ease in public.

One feature of the present invention is the extension of at least one slit opening, laterally from the proximal end to the distal end of the cylindrical body, to form a full slit on one side, and possibly a partial slit on another side. The full slit allows the insertion of a brush or a finger for thorough cleaning of the inside of the cylindrical body after use, thus giving a user the comfort that she or he may scrub all the surface inside if desired. The full slit also allows a tampon string to pass through when applying the tampon, thus minimizing the probability of accidentally latching the string in the applicator, or leaving the string in a crushed or tangled state, which makes the string difficult to catch when removing the tampon after use. The partial slit, on the other end, may be cut a few millimeters into the straight barrel, past the apex or the curved contour tip of the cylindrical body, to allow for the apex to open wide enough for the tampon to pass through in an intended straight direction, without forcing the tampon to lean towards the open full slit.

Another feature of the present invention is the use of medical grade or food grade silicone on the exterior surface of the cylindrical body to maximize user comfort, while also maximizing the flexibility of both the slit opening and the side slits for quick, comfortable tampon insertion and easy cleaning. Moreover, a rigid plastic material such as Nylon is used to form the interior of the barrel, possibly embedded entirely in the silicone layer, to provide solid support and facilitate tampon insertion. The silicone exterior and the plastic interior of the cylindrical body may be formed through co-molding or similar processes.

Yet another feature of the present invention is the minimal use of projections, protrusions, depressions, grooves, or other similar features for locking or securing separate components together. Such a minimalistic design is not only modern and iconic, it also provides a multitude of functional advantages. Firstly, potential pinching or slicing factor is minimized, making the reusable tampon applicator much more desirable than flimsy disposable tampon applicators. Secondly, potential blood pooling around such features is minimized, making the reusable tampon applicator easy to clean, even with bare fingers. Lastly, manufacturing cost may be reduced as surface contour complexity of the tampon applicator is lessened, making the present invention an economic supplement or substitute to currently available disposable tampon applicators, and perfect for use with washable tampons made from sea sponge, or knitted or crocheted from cotton or similar materials. The ease of manufacture, use, maintenance, and relative low cost may further enable the current invention to be deployed in developing countries, where hygienic menstrual products may help improve the quality of life of millions of women.

Moreover, while disposable tampons pre-packaged with disposable tampon applicators may be convenient to use, there have been instances of tainted moldy tampons found fresh out of the box. A user would not be able to visually examine the state of an enclosed tampon since such a tampon is exposed only during application or insertion. Bacteria contaminations pose consumer safety risks such as vaginal infections and pelvic inflammatory diseases that may significantly impact user health in both the short and the long terms. By comparison, reusable tampon applicators as disclosed herein allow separate storage of tampons and applicators, thus enabling a user to examine a tampon closely before tampon application and to discard visibly contaminated tampons if necessary.

THINX is a trademark name carrying embodiments of the present invention, and hence, the aforementioned trademark name may be interchangeably used in the specification and drawing to refer to products made according to various embodiments of the present invention. The term THINX may be used in this specification to describe any reusable tampon applicator as presented. With reference to the figures, embodiments of the present invention are now described in detail.

Figure 1C:
Figure 1D:
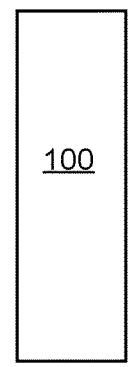

FIGS. 1A, 1B, 1C, and 1D show back, side, bottom, and front views respectively of a cover case 100 for a reusable tampon applicator, according to one embodiment of the present invention. In this illustrative example, cover case 100 is of a simple straight cylindrical shape, with a sealed flat surface 111 on a proximal end 110, and an open flat surface 131 with a base opening on a distal end 130. Barrel 120 is of a straight cylindrical shape and extends from proximal end 110 to distal end 130 to form cover case 100. When the tampon applicator is not in use, cover case 100 encloses other components of the tampon applicator, for hygienic and compact storage in a purse or a back pocket. Flat proximal and distal surfaces 111 and 131 allow cover case 100 to be stood up on either end, for easy placement on a counter-top, and for quick drying after a water rinse. In some embodiments, proximal surface 111 and distal surface 131 may be curved or shaped differently, and barrel 120 may be further contoured or curved. A bottom view as shown in FIG. 1C reveals a circular base opening in this particular illustrative example. In some embodiments, cross-sections of cover case 100 along different locations of barrel 120 may vary in shape. Cover case 100 may be made of flexible or rigid materials, and may comprise one or more materials such as silicone, plastics, metal, and fabrics.

FIGS. 2A, 2B, 2C, 2D, and 2E show back, side, bottom, sectional and front views respectively of a body 200 for a reusable tampon applicator, according to one embodiment of the present invention. In this illustrative example, body 200 is of a cylindrical shape, comprising a convex apex 215 on a proximal end 210, a hollow barrel portion 220, a transition portion 225, and a base grip portion 235 on a distal end 230. In some embodiments, transition portion 225 and base grip 235 are optional and excluded. When present, base grip 235 may have an external diameter larger than that of barrel 220, while curved transition portion 225 may taper to smoothly transit base grip 235 towards barrel portion 220. Such a design allows hygienic handling of the tampon applicator during use, as it enables a user to hold cylindrical body 200 at base grip 235 firmly without touching barrel 220, which in turn comes into contact with internal tissues during use.

While barrel 220 is of a straight cylindrical shape in this example, it may include a convex bulge or a concave narrowing in its upper, middle, or lower section in some other embodiments.

Although convex apex 215 is shown as rounded or spherical in FIGS. 2A, 2B, and 2E, in some other embodiments of the present invention, convex apex 215 may be acute, obtuse, or of any other convex shape that may facilitate easy insertion into a user's vagina during tampon application. A single slit opening 205 as shown in FIG. 2A cuts apex 215 into two separate pieces or "petals" 204, which may bend to allow a tampon to pass through slit opening 205 during tampon application. Furthermore, slit opening 205 may extend along barrel 220 laterally, down from proximal end 210 towards distal end 230 to form a partial slit 260 as shown in FIG. 2A, and from proximal end 210 to distal end 230 to form a full slit 270, as shown in FIG. 2E. In some embodiments, partial slit 260 cuts only a few millimeters into barrel 220, past convex apex 215. For example, partial slit 260 may cut 2 mm to 5 mm, 5 mm to 7 mm, or 7 mm to 10 mm into barrel 220, past convex apex 215. In some other embodiments, partial slit 260 may cut or extend through up to half of a lateral length of straight barrel 220. In yet some other embodiments, partial slit 260 may cut or extend through almost all of the lateral length of barrel 220. The partial slit is shorter in length along the cylindrical body than the full slit. In some other embodiments not shown here, more than one slits may intersect at the convex apex to form more than two petals, making the convex apex resemble a floret that can easily open during tampon application. Each slit opening may cut into the straight barrel portion at different depths. Moreover, as shown in FIG. 2A, a flat distal surface 231 on distal end 230 allows cylindrical body 200 to be stood up straight, for easy upright placement on a counter-top, and quick water drainage and drying after cleaning. In some other embodiments, distal surface 231 may be contoured or curved differently, with or without flat portions for upright placements.

More specifically, partial slit 260 as shown in FIGS. 2A and 2E allows slit opening 205 to open wide enough for a tampon to pass through in an intended straight direction during use, without forcing the tampon towards or out of open full slit 270 on the opposite side. Full slit 270 as shown in FIG. 2E allows the insertion of a brush or a finger for thorough cleaning of the inside of cylindrical body 200 after each use. Full slit 270 also allows a tampon string to pass through during tampon application, thus minimizing the probability of accidentally catching or latching the tampon string in the applicator, or leaving the tampon string in a crushed or tangled state, which may make the tampon string difficult to catch after tampon use. Moreover, curved corners 280 where full slit 270 and flat distal surface 231 join is contoured to maximize user safety and comfort. Similar curvatures may be further included in other corners, edges, rims, ridges, or similar features of the tampon applicator. As an example, FIGS. 11A to 13E provide an illustrative embodiment where individual curvatures are respectively labeled.

FIG. 2C shows a bottom view of cylindrical body 200. In this illustrative embodiment, a partial ring-shaped protrusion 243 is formed along the internal circumference of cylindrical body 200 at an appropriate lateral position. Partial ring-shaped protrusion 243 interfaces with a latch or notch 323 on a pusher 300 to tightly secure cylindrical body 200 and pusher 300 when not in use, as discussed with respect to FIG. 3A. Such a partial ring-shaped protrusion may be optional and excluded in some other embodiments not explicitly shown here.

FIG. 2D shows a sectional view of cylindrical body obtained along corresponding cutting planes A-A in FIG. 2B. In this illustrative embodiment, cylindrical body 200 comprises an outer layer 250 and an inner support layer 255. Inner support layer 255 is shown to be completely flush to outer layer 250. A smooth inner surface of cylindrical body 200 thus obtained allows a tampon to glide through easily. The inner and outer layers may be mechanically attached or bounded through a co-molding process such as co-injection molding or bi-injection molding. Outer layer 250 may fully extend over the entire exterior surface of cylindrical body 200, including barrel 220, convex apex 215, and optional transition portion 225 and grip portion 235. Partial slit 260 and full slit 270 as displayed in FIG. 2E are cut into outer layer 250. In some embodiments, outer layer 250 is made of a flexible biocompatible material such as medical grade or food grade silicone to reduce possible allergic reactions or immune responses when cylindrical body 200 comes into contact with internal tissues during use. In some embodiments, outer layer 250 is made of a hydrophobic or water-repellent material, or coated with such a layer, so blood or other body fluids are less likely to accumulate. Having a hydrophobic composition or coating also enables quick drying after a water rinse. In some embodiments, outer layer 250 is made of a water-proof or water impermeable material. In addition, outer layer 250 may be made flexible enough so petals 204 as shown in FIG. 2A open up during tampon application to allow a tampon to pass through slit opening 205. In addition, flexible folds or flaps 251 as shown in FIG. 2D allow full slit 270 to open slightly for easy washing and cleaning.

Furthermore, in this example, inner support layer 255 extends over an interior lateral surface of barrel 220. In the lateral direction, inner support layer 255 may cover the entirety or a portion of barrel 220. When optional transition portion 225 and base grip 235 as shown in FIG. 2A are present, inner support layer 255 as shown in FIG. 2D may extend fully or partially over the interior surface of these portions as well. Moreover, inner support layer 255 may open wider along full slit opening 270, as shown in FIG. 2D. This difference in slit opening widths forms folds or flaps 251.

In this illustrative example, inner support layer 255 is completely flush to outer layer 250. The smooth inner surface of cylindrical body 200 allow a tampon to glide through easily. In various embodiments, a portion or all of inner support layer 255 may be exposed and visible from the inner surface of cylindrical body 200, while being completely flush to outer layer 250. In some embodiments, inner support layer 255 may be completely embedded within outer layer 250, where inner support layer 255 is invisible from the inner surface of cylindrical body 200. The absence of part-lines between inner support layer 255 and outer layer 250 may ensure no blood or bacteria may be caught in between to cause any sanitation or hygiene problems.

In some embodiments, inner support layer 255 is made of natural or synthetic, hard, rigid or semi-rigid materials such as polymers, metals, and/or ceramics. For example, inner support layer 255 may be a plastic support made from polymeric materials such as Acrylonitrile butadiene styrene (ABS), Nylon, rubber, latex, and such.

In addition, although not shown explicitly in this example, inner support layer 255 may be patterned to include one or more additional lateral, helical, or rotational slits or cuts, so a cross-sectional view of cylindrical body 200 resembles a cut-open internal "gear" where the teeth are formed on the inner surface. The "gear" teeth may be parallel to or at an angle to the lateral axis of cylindrical body 200, similar to a spur gear, a helical gear, a worm gear, or such. A patterned inner support layer 255 as described may enhance the flexibility of cylindrical body 200 without significantly impacting its rigidity. Thus, a user may fully "unroll" cylindrical body 200 for thorough scrubbing and cleaning, while inner layer 255 still provides sufficient structural support for tampon insertion during use. A patterned inner support layer 255 may also serve as a movement guide for the tampon being applied. Moreover, in some embodiments where inner support layer 255 is patterned, slits or cuts within inner support layer 255 may be filled or injected with the same material as outer layer 250, so inner support layer 255 is either flush to outer layer 250 on the inner surface of cylindrical body 200, or completely embedded within outer layer 250.

Figure 3A:
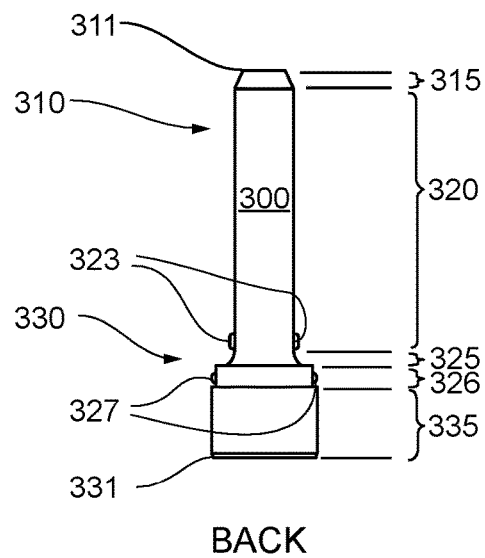
FIGS. 3A, 3B, 3C, and 3D show back, side, bottom, and front sides of a pusher for the reusable tampon applicator respectively, according to one embodiment of the present invention.
Figure 3B:
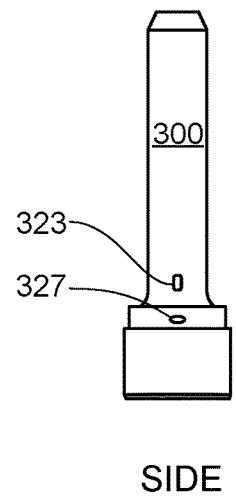
Figure 3C:
Figure 3D:
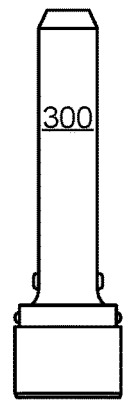

FIGS. 3A, 3B, 3C, and 3D show back, side, bottom, and front views of a pusher 300 for a reusable tampon applicator respectively, according to one embodiment of the present invention. In this illustrative example, pusher 300 as shown in FIG. 3A comprises a cylindrical straight barrel portion 320 extending from a proximal end 310 to a distal end 330. Optionally, pusher 300 further comprises one or more of a conical pyramid-shaped tip 315 at proximal end 310, a transition portion 325 at a distal end 330 of straight barrel 320, a step transition portion 326, and a base grip portion 335 at distal end 330. Conical pyramid-shaped tip 315 may comprise a flat proximal surface 311 for exerting force on a tampon during tampon application. When present, base grip 335 may have an external diameter larger than or smaller than that of straight barrel 320 and step transition portion 326. Similarly, step transition portion 326 may have a diameter larger than or smaller than that of straight barrel 320. Depending on the diameters of step transition portion 326 and straight barrel 320, transition portion 325 may taper appropriately to smoothly transit between the two portions. Transition portion 325, step transition portion 326, and base grip portion 335 may also be excluded entirely. Base grip portion 335 allows hygienic handling of the tampon applicator during use, as it enables a user to hold pusher 300 firmly without touching straight barrel 320, which comes into contact with the tampon and cylindrical body 200 during tampon application. In some embodiments, a flat distal surface 331 of pusher 300 allows pusher 300 to be stood up straight, for easy upright placement on a countertop, and quick water drainage and drying after cleaning. In some other embodiments, distal surface 331 may be contoured or curved differently, with or without flat portions for upright placement. In yet some other embodiments, bottom view as shown in FIG. 3C may be of square, rectangular, stellar, or any other shape.

Furthermore, one or more bumps, latches or notches such as 323 and 327 shown in FIG. 3A may be present, for tightly securing pusher 300, cylindrical body 200, and/or case 100 when the tampon applicator is not in use. It would be understood by persons skilled in the art that the drawings are not necessarily drawn to scale, thus notches 323 and 327 may raise or bump above the lateral surface only minimally. In some embodiments, corresponding individual or ring-shaped depressions, dents, grooves or protrusions may be present on an internal surface of cylindrical body 200 and/or case 100 for interfacing or clicking onto the notches as shown. Such notches and/or depressions may be located symmetrically or asymmetrically around the internal lateral circumferences of straight barrel 220, internal lateral circumferences of case 100, or external lateral circumferences of straight barrel 320 and step transition portion 326. In yet some other embodiments, neither notches nor depressions may be present, and various internal and external diameters of case 100, body 200, and pusher 300 may be carefully designed so that a tight and secure assembly can be achieved.

Figure 4A:
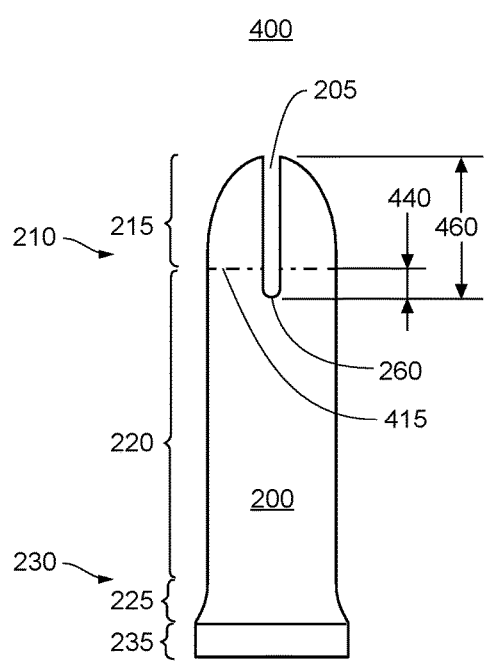
FIGS. 4A and 4B show back and front sides of a body for a reusable tampon applicator respectively, as enlarged views of FIGS. 2A and 2E, according to one embodiment of the present invention.

Corresponding to FIGS. 2A and 2E, FIGS. 4A and 4B show a back side view 400 and a front side view 450 of cylindrical body 200 respectively, according to one embodiment of the present invention. As discussed previously, in this illustrative example, cylindrical body 200 comprises a convex apex 215 on a proximal end 210, a barrel portion 220, an optional tapered transition portion 225, and an optional base grip portion 235 on a distal end 230. Dotted line 415 in FIG. 4A represents an adjoining boundary between convex apex 215 and straight barrel 220. Slit opening 205 extends along straight barrel 220 laterally or longitudinally, down from proximal end 210 towards distal end 230 to form partial slit 260 shown in FIG. 4A, with a length 460, and from proximal end 210 to distal end 230 to form full slit 270 shown in FIG. 4B, with a length 470. In various embodiments, the ratio of length 460 to length 470 is between 1:10 and 2:7, between 2:7 and 1:3, between 1:3 and 1:2, or between 1:2 and 19:20, either inclusively or exclusively. In some embodiments, partial slit 260 does not cut into straight barrel 220. Thus, length 440 shown in FIG. 4A, which measures the section of partial slit 260 pass boundary line 415, is equal to zero. In some other embodiments such as shown here, partial slit 260 cuts into straight barrel 220, and length 440 is between 2 mm to 5 mm, 5 mm to 7 mm, 7 mm to 10 mm, or is more than 10 mm. Partial slit 260 is shorter in length than full slit 270.

Figure 4B:
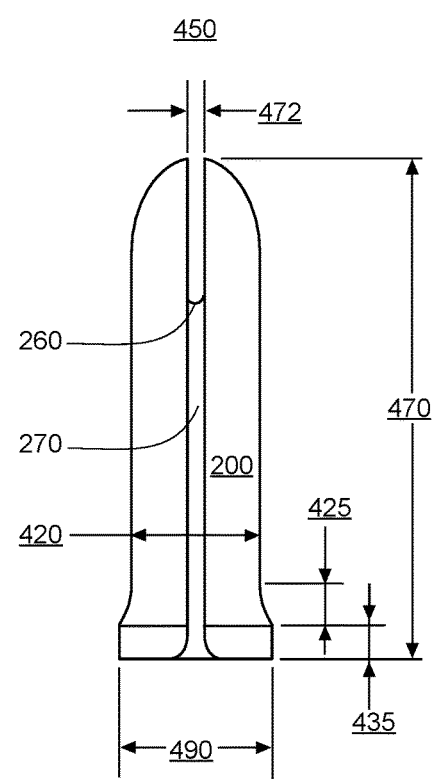

In front side view 450 shown in FIG. 4B, partial slit 260 and full slit 270 have the same uniform width 472. In some other embodiments, slit width may differ between partial slit 260 and full slit 270, and slit width 472 may vary along the lateral side of cylindrical body 200. For example, slit width 472 may be larger towards the proximal end to facilitate easy tampon expulsion, or may be larger towards the distal end to make cleaning easier. In addition, straight barrel portion 220 from FIG. 4A is shown to have a uniform external diameter 420 in FIG. 4B. In some embodiments, external diameter 420 may vary laterally along cylindrical body 200. For example, barrel portion 220 may comprise a convex bulge in its upper, middle, or lower section, with a narrower convex apex 215 and/or a narrower base grip portion 235, or may comprise a concave narrowing in its upper, middle, or lower section, with a wider convex apex 215 and/or a wider base grip portion 235. Base grip portion 235 has an external diameter 490 in this illustration example. As previously discussed, transition portion 225 with length 425 smoothly transits straight barrel portion 220 into base grip portion 235 with length 435. Each of lengths 425 and 435 may vary between zero and a third of length 470. An external base grip diameter 490 larger than an external barrel diameter 420 allows a user to hold cylindrical body 200 firmly without touching barrel portion 220. In some other embodiments not shown explicitly here, external base grip diameter 490 may be smaller than external barrel diameter 420, with transition portion 225 curving into instead of curving out to base grip portion 225. Such a design may help trap the tampon once disposed inside cylindrical body 200, thus avoiding accidentally dropping the tampon during tampon application.

Figure 5A:
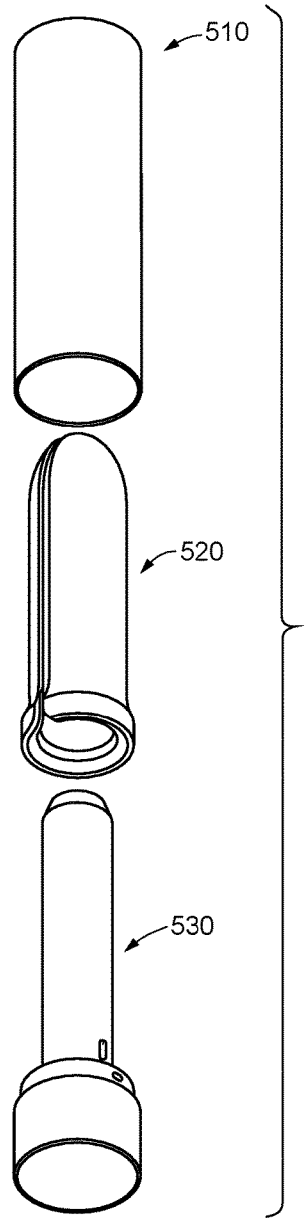
FIG. 5A shows an exploded perspective view of a reusable tampon applicator having the case, the body, and the pusher shown in FIGS. 1A, 2A, and 3A respectively, according to one embodiment of the present invention.

FIG. 5A shows an exploded perspective view 500 of a reusable tampon applicator, having the case, the body, and the pusher shown in FIGS. 1A, 2A, and 3A respectively, according to one embodiment of the present invention. Case 510, cylindrical body 520, and pusher 530 are as described with respect to FIGS. 1A to 4B. Each of case 510, cylindrical body 520, and pusher 530 may be manufactured with an injection molding process. A co-molding process may also be employed to form or bound outer and inner layers of cylindrical body 520. In addition, case 510 and at least a segment of pusher 520 may be made of stamped metal, without injection molding.

Figure 5B:
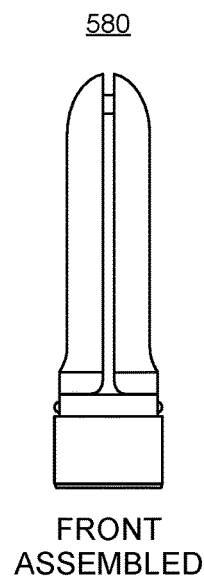
FIGS. 5B and 5C show respective assembled views of the reusable tampon applicator in FIG. 5A, according to one embodiment of the present invention.
Figure 5C:
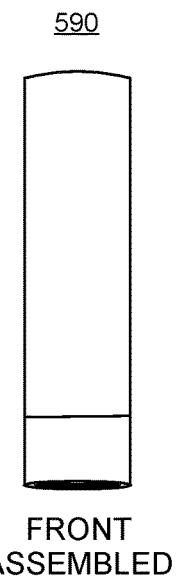
Figure 5D:
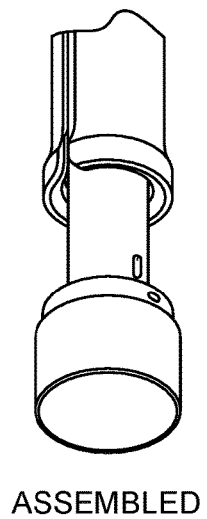
FIGS. 5D and 5E show respective zoomed-in assembled views of the reusable tampon applicator in FIG. 5A, according to one embodiment of the present invention.
Figure 5E:
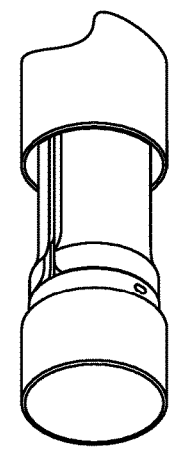

FIG. 5B shows a front view of an assembly 580 when pusher 530 is telescopically inserted into cylindrical body 520, while FIG. 5C shows another front view of an assembly 590 when case 510 encloses the assembly 580. FIGS. 5D and 5E zoom into assembled views in FIGS. 5B and 5C respectively around the distal end of the tampon applicator, showing optional notches for securing individual components together.

Use of the Reusable Tampon Applicator

FIGS. 6A, 6B, 6C, and 6D illustrate the use of a reusable tampon applicator for disposing a tampon into the tampon applicator, and inserting the tampon into a user's body, according to one embodiment of the present invention. More specifically, FIG. 6A presents an assembled tampon applicator 610 ready for use or storage. After the cover case is removed, FIG. 6B illustrates a pulling action to remove the telescopically inserted pusher 630 from cylindrical body 620. Next, a tampon 640 as shown in FIG. 6C may be inserted by a user into cylindrical body 620, followed by pusher 630. Tampon string 645 maybe positioned along full slit 670 shown in FIG. 6D during this process. The assembled pusher-tampon-body may then be inserted into the vaginal opening, and force may be exerted through pusher 630 to expulse or eject tampon 640 through the slit opening on the proximal end of cylindrical body 620, as illustrated by FIG. 6D. "Petals" 604 and 606 formed by the slit opening open or bend outward to allow tampon 640 to pass through, and tampon string 645 may glide along full slit 670 in this process. Such a full slit design minimizes the probability of accidentally catching the string in the applicator, or leaving the tampon string in a crushed or tangled state, which may make the tampon string difficult to catch after tampon use. Once tampon 640 has been applied or inserted successfully, the remaining pusher-body assembly may be removed from the vagina, disassembled, and cleaned, before being enclosed by a cover case and stored away.

Alternative Embodiments

Figure 7A:
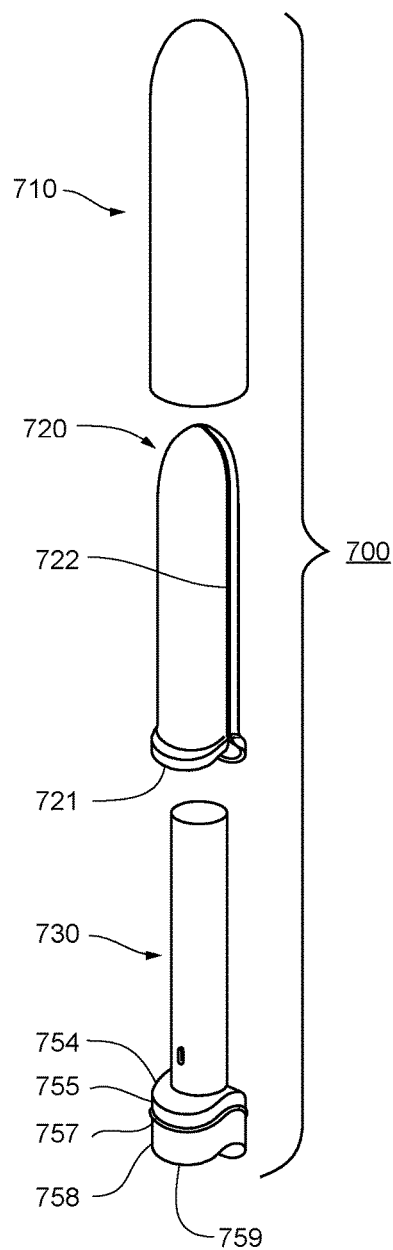
FIGS. 7A and 7B show exploded and assembled views of a reusable tampon applicator respectively, according to a second embodiment of the present invention.
Figure 7B:
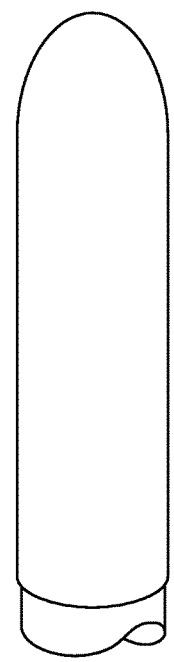
Figure 7C:
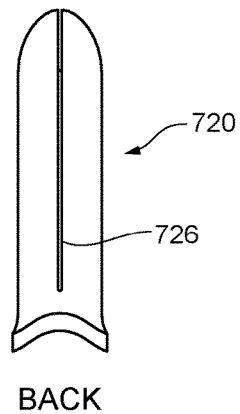
FIG. 7C shows a back view of the exemplary reusable tampon applicator body in FIG. 7A.

FIG. 7A shows an exploded perspective view 700 of a reusable tampon applicator, according to a second embodiment of the present invention, with case 710, cylindrical body 720, and pusher 730. FIG. 7B shows a corresponding assembled view 750, and FIG. 7C shows a back view of cylindrical body 720. In this particular embodiment, case 710 is flat on the distal end, but convexly curved on the proximal end. It would be clear to ones skilled in the art that case 710 may take on any shape as long as it is capable of enclosing the body and pusher portions of a reusable tampon applicator as disclosed. In addition, in this particular embodiment, cylindrical body 720 as shown in FIGS. 7A and 7C comprises a full slit 722 extending from the proximal end to the distal end, and a partial slit 726 extending from the proximal end towards the distal end, where a ratio of lengths between the partial slit and the full slit may be in the range between 1:2 to 2:3, and 2:3 to 19:20. Distal surface 721 of cylindrical body 720 is curved in this particular example. Moreover, while pusher 730 excludes a curved transition portion, it may contain a seat portion 755 with curved proximal surface 754 that locks with distal surface 721 of cylindrical body 720. Pusher 730 may further comprise decorative components such as surface line 757, while base grip 758 may comprise a curved distal surface 759.

FIG. 8A shows an exploded perspective view 800 of a reusable tampon applicator, according to a third embodiment of the present invention, with case 810, cylindrical body 820, and pusher 830. FIG. 8B shows a corresponding assembled view 850. FIGS. 8C and 8D show top views 825 and 835 of cylindrical body 820 and pusher 830 respectively. In this particular embodiment, case 810 is slanted on the distal end, and convexly curved on the proximal end. Cylindrical body 820 comprises a full slit 827, and a partial slit on the opposite side. Pusher 830 may be hollow, with a proximal opening 831 through which a tampon string can be inserted or threaded. A full slit 837 on one side of pusher 830 also allows the tampon string to pass through. A circular rim 832 may serve as a tightening notch to secure pusher 830 and body 820 together when the tampon applicator is not in use. Furthermore, in this example, base grip 833 has a contoured distal surface 834.

FIG. 9A shows an exploded perspective view 900 of a reusable tampon applicator, according to a fourth embodiment of the present invention, with case 910, cylindrical body 920, and pusher 930. FIG. 9B shows a corresponding assembled view 950. FIGS. 9C and 9D show top views 925 and 935 of cylindrical body 920 and pusher 930 respectively. In this particular embodiment, case 910 is flat on both the distal end and the proximal end, and has decagon-shaped cross-sections. Similarly, cylindrical body 920 also has decagon-shaped cross-sections. In some other embodiments, case 910, cylindrical body 920, and pusher 930 may have cross-sections shaped as regular or non-regular polygons with any number of edges. In addition, in this particular embodiment, cylindrical body 920 does not include any full lateral slits. Instead, more than one slit openings are cut on convex apex 922 to form a floret containing more than two petals. As shown in FIG. 9C, five petals including petal 928 are present in this particular example. Pusher 930, on the other hand, has a spoked cross-section, illustrated by FIG. 9D. In some embodiments, slit openings on convex apex 922 may extend and cut into the barrel portion of body 920, at the same or different lengths or depths.

Reusable Tampon Applicator Hygiene Pack

Figure 10:
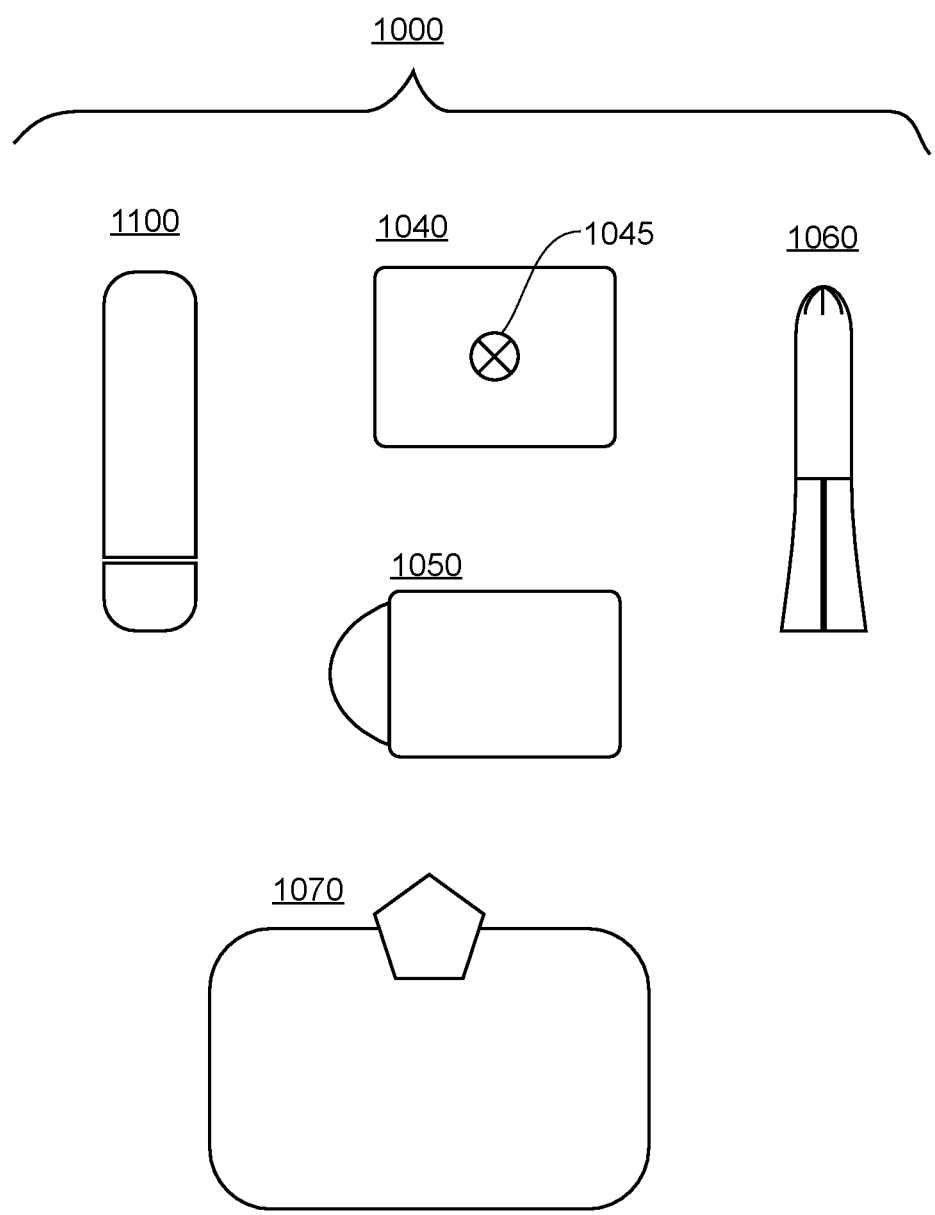
FIG. 10 shows a reusable tampon applicator hygiene pack, according to one embodiment of the present invention.

FIG. 10 shows a THINX reusable tampon applicator hygiene pack 1000, according to one embodiment of the present invention. While a THINX reusable tampon applicator 1100 as described previously with references to FIGS. 1A to 9D may be carried and used individually, it may also be combined with one or more other optional accessories such as biodegradable films 1040, biodegradable wipes 1050, a tampon 1060 with a built-in film, and a clutch or carrying purse 1070. A biodegradable film 1040 may be used to cover the entire tampon applicator body before tampon insertion, during which a tampon pushes through a perforation. Biodegradable film 1040 may be disposable to provide a convenient and hygienic way of minimizing direct contact of the reusable tampon applicator with blood or other body fluids. A tampon 1060 with a build-in film may be made of organic cotton packed and wrapped with a hygienic, bio-compatible film that extends beyond the body of the tampon, to offer additional hygienic protection by minimizing direct contact of the tampon with the inside surface of the cylindrical body of a reusable tampon applicator. Biodegradable wipe 1050 may be made of organic cotton and pre-moistened to provide a portable and disposable solution for cleaning and refreshing the user's hands or the reusable tampon applicator before and/or after a tampon change. Moreover, clutch or carrying purse 1070 may be compartmentalized to store any of reusable tampon applicator 1010, biodegradable films 1040, biodegradable wipes 1050, and tampon 1060.

Illustrative Example

With reference to the figures, the following are perspective and sectional views of an exemplary embodiment, illustrated with typical line styles and types for engineering design drawings. These figures are not necessarily drawn to exact scale, with emphasis instead being placed on illustrating various aspects of the devices and methods described herein. Device dimensions such as lengths, radii, diameters, and opening angles are individually labeled for this particular exemplary embodiment, where appropriate. More specifically, diameters are preceded by symbol Ø, radii for curvatures are preceded by symbol R, and all dimensions are presented in metric units of millimeters (mm). Conversions to inches or other non-metric units would be readily apparent to one of ordinary skill in the art. It would be further understood by those of ordinary skill in the art that the shown dimensions are exemplary only, and any suitable variations may be used in similar embodiments, as long as the functional structure of the present invention is maintained.

Figure 11A:
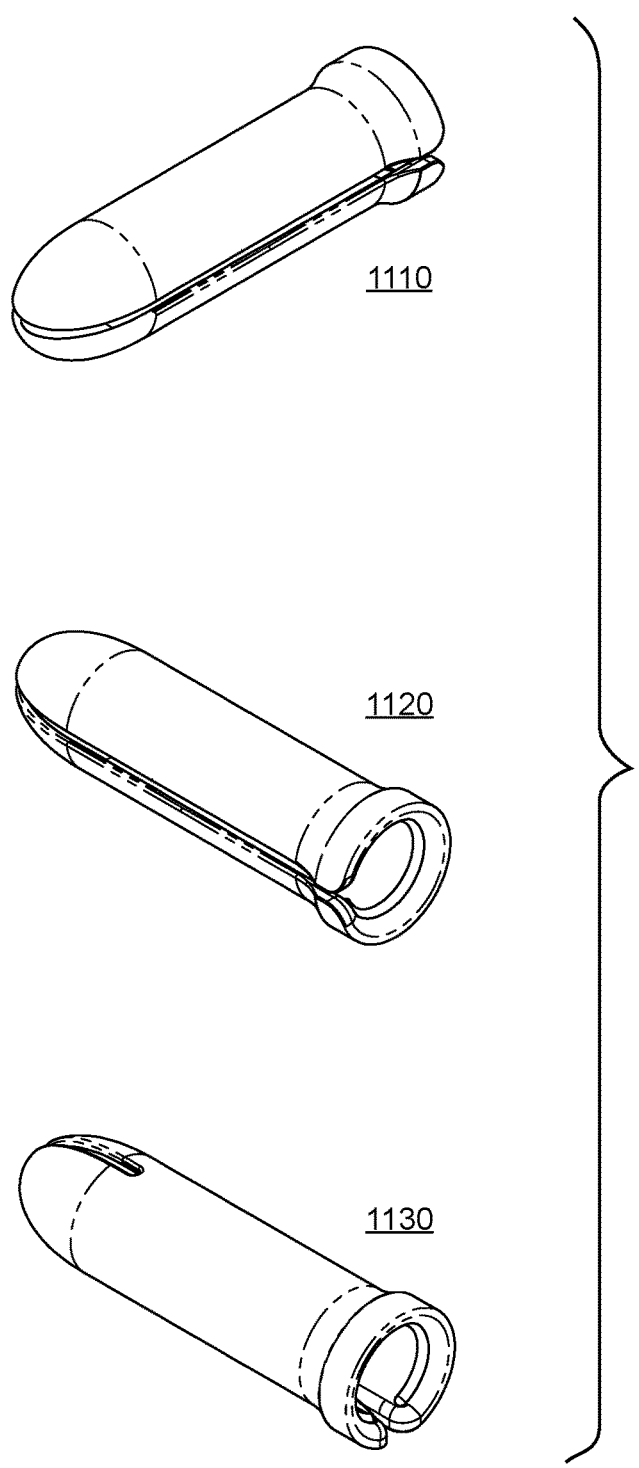
FIG. 11A shows perspective views of an exemplary applicator body, according to one embodiment of the present invention.
Figure 11B:
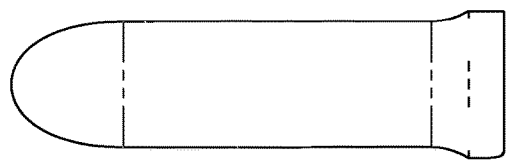
FIGS. 11B, 11C, 11D, 11E, 11F, 11G, 11H, and 11J show respective side and sectional views of the exemplary applicator body in FIG. 11A, with illustrative dimensions.
Figure 11C:
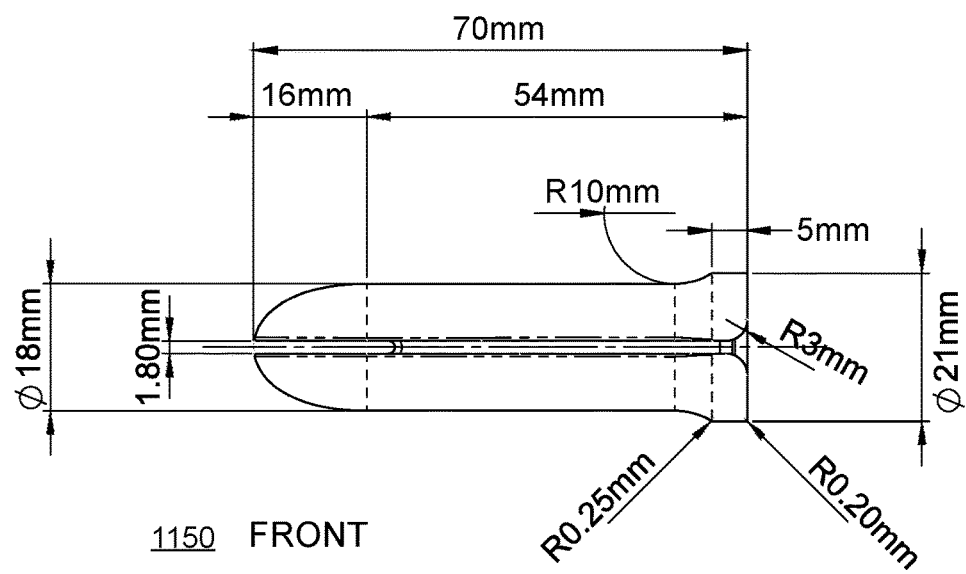

FIG. 11A shows three perspective views 1110, 1120, and 1130 of an exemplary applicator body, according to one embodiment of the present invention. Following general engineering drawing protocols, part outlines and section lines are solid, while hidden lines are dotted. A full slit is visible in perspective views 1110 and 1120, while a partial slit is visible in perspective view 1130.

Figure 11D:
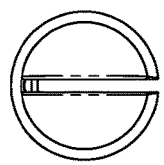
Figure 11E:
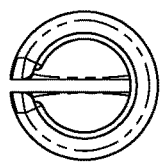
Figure 11F:
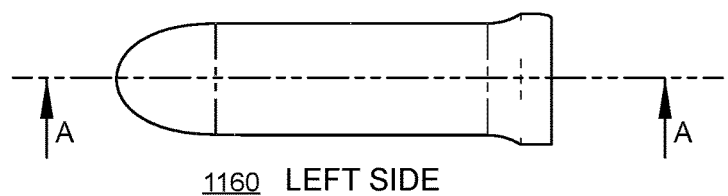
Figure 11G:
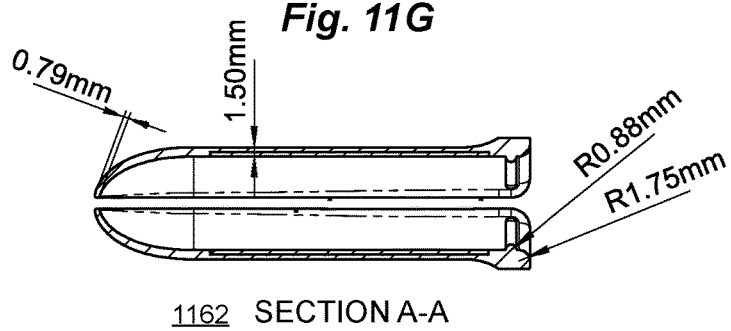
Figure 11H:
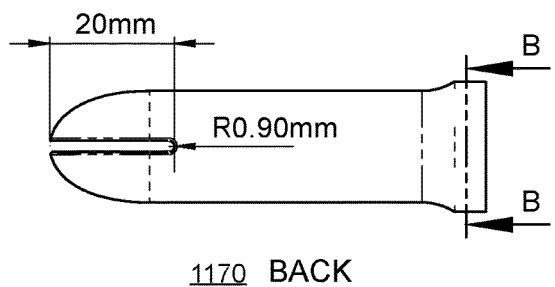
Figure 11J:
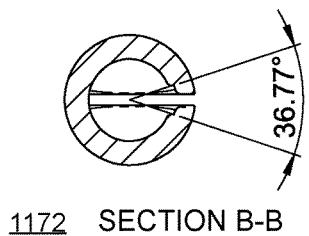

FIGS. 11B, 11C, 11D, 11E, 11F, 11G, 11H, and 11J show respective different side and sectional views of the exemplary applicator body in FIG. 11A, with illustrative dimensions where appropriate. Side views 1140 in FIG. 11B and 1160 in FIG. 11F, front view 1150 in FIG. 11C, bottom view 1154 in FIG. 11E, and back side view 1170 in FIG. 11H are similar to the ones shown in FIGS. 2A, 2B, 2C, and 2E. Top view 1152 in FIG. 11D is obtained by looking down the convex apex of the cylindrical body, bottom view 1154 in FIG. 11E is obtained by looking up the distal base opening of the cylindrical body, while sectional views 1162 in FIG. 11G and 1172 in FIG. 11J are obtained along corresponding cutting planes A-A and B-B shown in FIGS. 11F and 11H. It is easy to see from FIGS. 11C and 11H that in this example, the partial lateral slit exceeds the lateral length of the convex apex by 4 mm, in a range between 2 mm and 5 mm. The partial lateral slit and full lateral slit has a ratio in length of 2:7 (20 mm:70 mm), in a range between 1:10 and 2:7 inclusive. In addition, as shown by sectional view 1162 in FIG. 11G, the exemplary cylindrical body has a thickness of 0.79 mm at the tip along the slit opening, and a thickness of 1.50 mm along the length of the straight barrel portion.

Figure 12A:
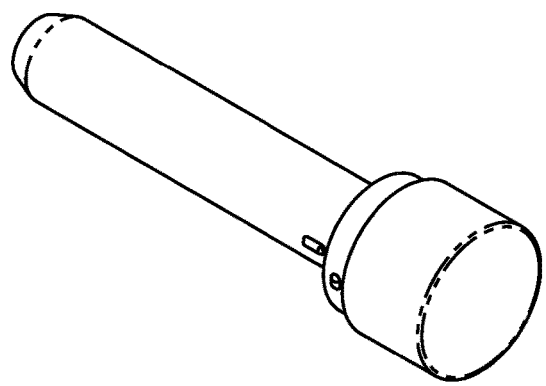
FIG. 12A shows a perspective view of an exemplary pusher, according to one embodiment of the present invention.
Figure 12B:
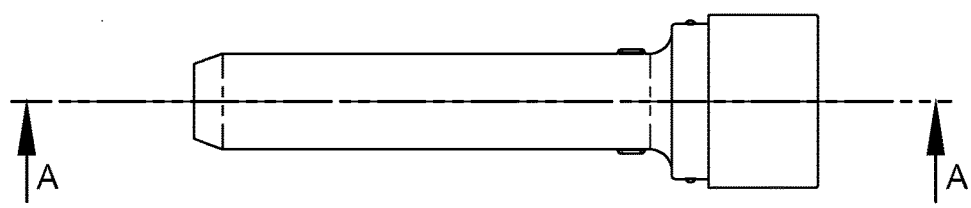
FIGS. 12B, 12C, 12D, 12E, and 12F show respective side and sectional views of the exemplary pusher in FIG. 12A, with illustrative dimensions.
Figure 12C:
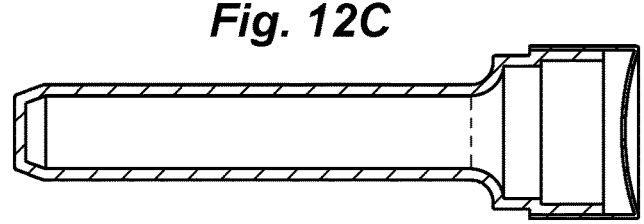
Figure 12D:
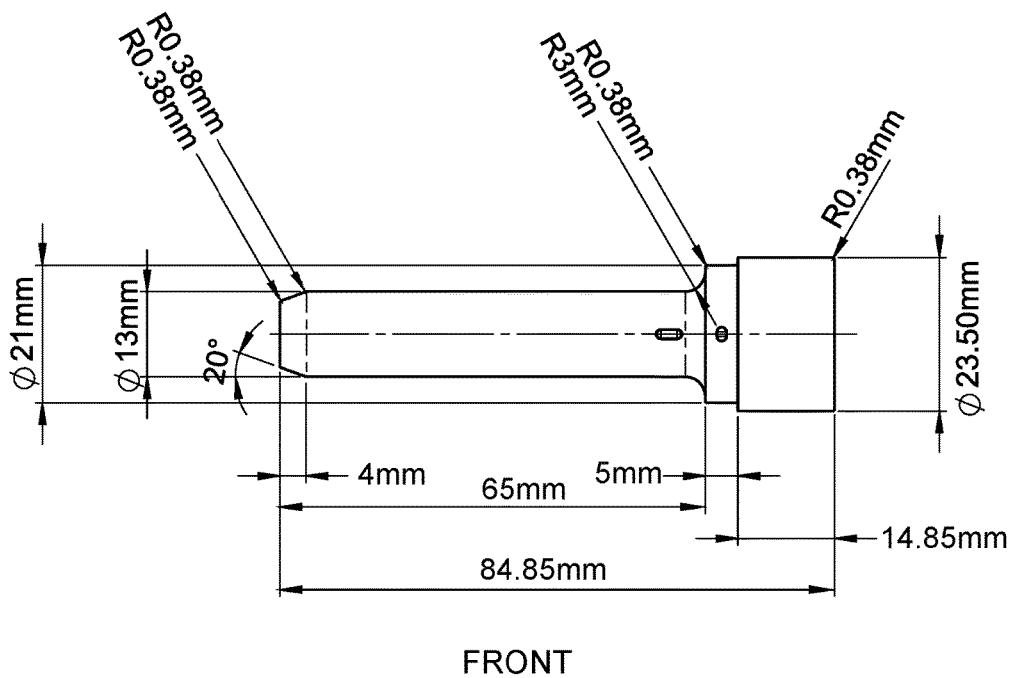
Figure 12E:
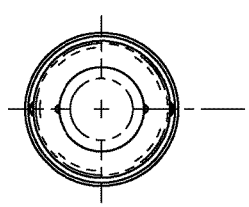
Figure 12F:
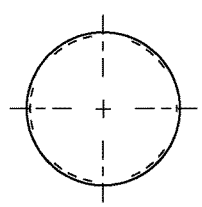

FIG. 12A shows a perspective view of an exemplary pusher, according to one embodiment of the present invention. Correspondingly, FIGS. 12B, 12C, 12D, 12E, and 12F show respective side and sectional views of the exemplary pusher in FIG. 11A, with illustrative dimensions where appropriate.

Figure 13A:
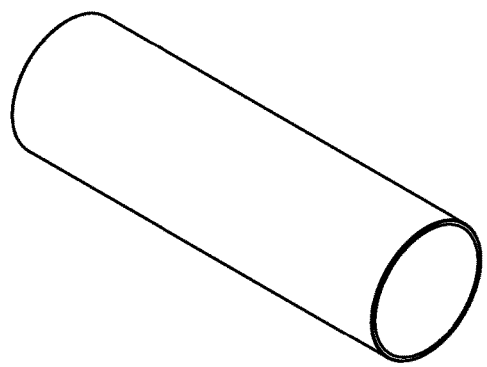
FIG. 13A shows a perspective view of an exemplary case, according to one embodiment of the present invention.
Figure 13B:
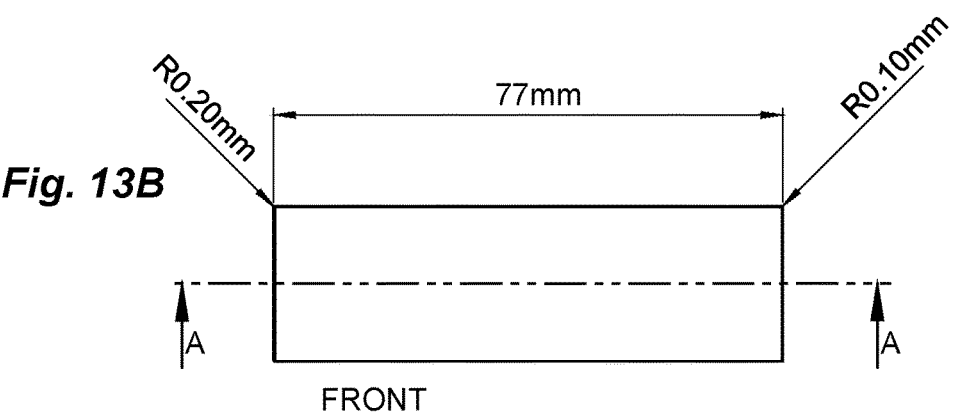
FIGS. 13B, 13C, 13D, and 13E show respective side and sectional views of the exemplary case in FIG. 13A, with illustrative dimensions.
Figure 13C:
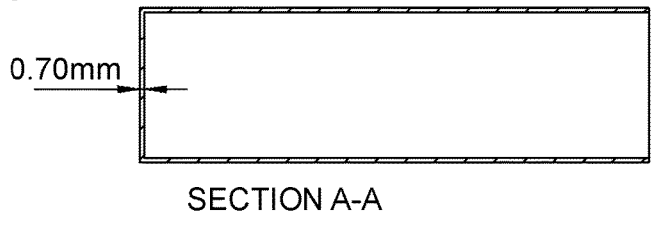
Figure 13D:
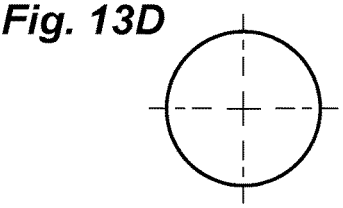
Figure 13E:
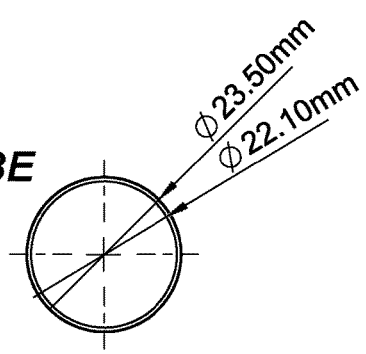

Finally, FIG. 13A shows a perspective view of an exemplary case, according to one embodiment of the present invention. Correspondingly, FIGS. 13B, 13C, 13D, and 13E show respective side and sectional views of the exemplary case in FIG. 13A, with illustrative dimensions where appropriate.

One of ordinary skill in the art knows that the use cases, structures, schematics, and diagrams may be constructed or performed in other combinations or orders, but the inventive concept of the present invention remains without departing from the broader scope of the invention. Every embodiment may be unique, and constituting components may be either shortened or lengthened, narrowed or widened; methods and steps may also be shortened or lengthened, overlapped with other activities, postponed, delayed, and continued after a time gap, during the practice of the present invention.

Although the present invention has been described with reference to specific exemplary embodiments, it will be evident that the various modification and changes can be made to these embodiments without departing from the broader scope of the invention. Accordingly, the specification and drawings are to be regarded in an illustrative sense rather than in a restrictive sense. It will also be apparent to the skilled artisan that the embodiments described above are specific examples of a single broader invention which may have greater scope than any of the singular descriptions taught. There may be many alterations made in the descriptions without departing from the scope of the present invention as defined by the appended claims.

What is claimed is:

1. A reusable tampon applicator, comprising:
    a hollow cylindrical body for holding a tampon for tampon application, the cylindrical body comprising a distal end and a proximal end, and a base opening at the distal end for inserting the tampon into a straight barrel connected to a convex apex at the proximal end,
        wherein the cylindrical body comprises a transition portion and a base grip portion at the distal end,
        wherein an external diameter of the base grip portion is larger than an external diameter of the straight barrel,
        wherein the convex apex comprises a slit opening for the tampon to pass through during tampon application,
        wherein the slit opening extends from the proximal end to the distal end to form a full slit on a first lateral side of the cylindrical body, and
        wherein the slit opening extends from the proximal end towards the distal end to form a partial slit on a second lateral side of the cylindrical body, opposite to the first lateral side of the cylindrical body, wherein the partial slit is shorter in length along the cylindrical body than the full slit; and
    a pusher, for telescopic insertion into the cylindrical body, and for pushing the tampon out from the slit opening during tampon application.

2. The reusable tampon applicator of claim 1, further comprising:
    a case for telescopically enclosing the cylindrical body and the pusher.

3. The reusable tampon applicator of claim 1, wherein the partial slit on the second lateral side of the cylindrical body extends beyond the apex into the straight barrel for a length between 2 mm and 5 mm.

4. The reusable tampon applicator of claim 1, wherein a ratio of lengths between the partial slit and the full slit is between 1:10 and 2:7.

5. The reusable tampon applicator of claim 1, wherein a ratio of lengths between the partial slit and the full slit is between 2:7 and 1:3.

6. The reusable tampon applicator of claim 1, wherein the cylindrical body comprises an outer silicone layer and an inner support layer, and wherein the outer silicone layer extends fully over an exterior surface of the cylindrical body.

7. The reusable tampon applicator of claim 6, wherein the inner support layer extends partially over an interior lateral surface of the cylindrical body, and wherein the inner support layer is enclosed fully by the outer silicone layer.

8. The reusable tampon applicator of claim 6, wherein the inner support layer is made of a plastic material is selected from the group consisting of acrylonitrile butadiene styrene (ABS) plastic and nylon plastic.

9. The reusable tampon applicator of claim 1, wherein the pusher comprises at least one notch on an external lateral surface for securing the cylindrical body and the pusher while not in use.

10. The reusable tampon applicator of claim 1, wherein the distal end of the cylindrical body comprises a flat base surface, the flat base surface for standing the cylindrical body on a flat surface.

11. The reusable tampon applicator of claim 1, wherein a distal end of the pusher comprises a flat base surface, the flat base surface for standing the pusher on a flat surface.

12. The reusable tampon applicator of claim 1, wherein the pusher further comprises:
a main cylindrical portion, and a base grip portion at a distal end of the pusher,
wherein an external diameter of the main cylindrical portion is smaller than an internal diameter of the base opening of the cylindrical body, and
wherein an external diameter of the base grip portion is larger than the internal diameter of the base opening of the cylindrical body.

13. A method for making a reusable tampon applicator, comprising the steps of:
bounding an inner support layer and an outer silicone layer of a hollow cylindrical body, the cylindrical body comprising a distal end and a proximal end,
wherein the cylindrical body comprises a transition portion and a base grip portion at the distal end,
wherein an external diameter of the base grip portion is larger than an external diameter of the straight barrel,
wherein the distal end comprises a base opening for inserting a tampon into the cylindrical body,
wherein the proximal end comprises a convex apex with a slit opening for the tampon to pass through during tampon application,
wherein the slit opening extends from the proximal end to the distal end on a first lateral side of the cylindrical body to form a full slit, and
wherein the slit opening extends partially from the proximal end towards the distal end on a second lateral side of the cylindrical body, opposite to the first lateral side of the cylindrical body, to form a partial slit, wherein the partial slit is shorter in length along the cylindrical body than the full slit; and
forming a cylindrical pusher, for telescopic insertion into the cylindrical body, and for pushing the tampon through the slit opening during tampon application.

14. The method of claim 13, wherein the inner support layer extends partially over an interior lateral surface of the cylindrical body, and wherein the inner support layer is enclosed fully by the outer silicone layer.

15. The method of claim 13, wherein the partial slit on the second lateral side of the cylindrical body extends beyond the apex into the straight barrel for a length between 2 mm and 5 mm.

16. The method of claim 13, wherein the outer silicone layer extends fully over an exterior lateral surface of the cylindrical body.

17. The method of claim 13, wherein a ratio of lengths between the partial slit and the full slit is between 1:10 and 2:7.

18. The method of claim 13, wherein a ratio of lengths between the partial slit and the full slit is between 2:7 and 1:3.

19. An article of manufacture for a reusable tampon applicator, comprising:
a distal end and a proximal end, and a base opening at the distal end for inserting a tampon into a straight barrel connected to a convex apex at the proximal end,
wherein the convex apex comprises a slit opening for the tampon to pass through during tampon application,
wherein the slit opening extends from the proximal end to the distal end to form a full slit on a first lateral side of the cylindrical body, and
wherein the slit opening extends from the proximal end towards the distal end to form a partial slit on a second lateral side of the article, opposite to the first lateral side of article, wherein the partial slit is shorter in length along the cylindrical body than the full slit; and
a transition portion and a base grip portion at the distal end, wherein an external diameter of the base grip portion is larger than an external diameter of the straight barrel.

* * * * *